(12) United States Patent
Sheth et al.

(10) Patent No.: US 11,776,126 B2
(45) Date of Patent: Oct. 3, 2023

(54) SYSTEMS AND METHODS FOR EVALUATING THE BRAIN AFTER ONSET OF A STROKE USING COMPUTED TOMOGRAPHY ANGIOGRAPHY

(71) Applicant: The Board of Regents, The University of Texas System, Austin, TX (US)

(72) Inventors: Sunil A. Sheth, Houston, TX (US); Luca Giancardo, Houston, TX (US); Sean I. Savitz, Houston, TX (US)

(73) Assignee: The Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 17/752,718

(22) Filed: May 24, 2022

(65) Prior Publication Data
US 2022/0284581 A1 Sep. 8, 2022

Related U.S. Application Data (63) Continuation of application No. 16/572,564, filed on Sep. 16, 2019, now Pat. No. 11,341,647.
(Continued)

(51) Int. Cl.
*G06K 9/00* (2022.01)
*G06T 7/00* (2017.01)
(Continued)

(52) U.S. Cl.
CPC ........ *G06T 7/0016* (2013.01); *A61B 5/02042* (2013.01); *A61B 5/4842* (2013.01); *A61B 5/7267* (2013.01); *A61B 5/7275* (2013.01); *A61B 6/032* (2013.01); *A61B 6/501* (2013.01); *A61B 6/504* (2013.01); *A61B 6/507* (2013.01); *G06N 3/04* (2013.01); *G06N 3/08* (2013.01); *G06T 11/003* (2013.01); *G16H 30/40* (2018.01); *G06T 2207/10081* (2013.01); *G06T 2207/20084* (2013.01); *G06T 2207/30016* (2013.01); *G06T 2207/30101* (2013.01)

(58) Field of Classification Search
None
See application file for complete search history.

(56) References Cited

U.S. PATENT DOCUMENTS

2014/0257094 A1* 9/2014 Meetz .................... G16H 50/30
600/431
2016/0180042 A1 6/2016 Menon et al.
(Continued)

OTHER PUBLICATIONS

Muschelli, et al. "Validated Automatic Brain Extraction of Head CT Images" Neuroimage 114, 379-385 (2015).
(Continued)

*Primary Examiner* — Wei Wen Yang
(74) *Attorney, Agent, or Firm* — Thomas Horstemeyer, LLP (57) ABSTRACT

In one embodiment, a patient's brain is evaluated after onset of a stroke by capturing computed tomography angiography (CTA) images of the brain, analyzing the CTA images with a CTA image analysis program to evaluate the patient's brain, and generating results based upon the analysis that provide an assessment of the brain. In some cases, the CTA image analysis program comprises a machine-learning algorithm that has been trained on the results of perfusion imaging analysis.

3 Claims, 8 Drawing Sheets

Related U.S. Application Data (60) Provisional application No. 62/731,108, filed on Sep. 14, 2018.

(51) Int. Cl.

| | |
|---|---|
| *G06N 3/08* | (2023.01) |
| *G06N 3/04* | (2023.01) |
| *G16H 30/40* | (2018.01) |
| *A61B 6/03* | (2006.01) |
| *A61B 6/00* | (2006.01) |
| *A61B 5/00* | (2006.01) |
| *A61B 5/02* | (2006.01) |
| *G06T 11/00* | (2006.01) |

(56) References Cited

U.S. PATENT DOCUMENTS

| | | |
|---|---|---|
| 2017/0300654 A1 | 10/2017 | Stein et al. |
| 2018/0182096 A1 | 6/2018 | Grady et al. |
| 2019/0244348 A1 | 8/2019 | Buckler et al. |

OTHER PUBLICATIONS

Jovin, T. G. et al. Diffusion-weighted imaging or computerized tomography perfusion assessment with clinical mismatch in the triage of wake up and late presenting strokes undergoing neurointervention with Trevo (DAWN) trial methods. Int J Stroke 12, 641-652 (2017).

Albers, G. W. et al. A multicenter randomized controlled trial of endovascular therapy following imaging evaluation for schemic stroke (DEFUSE 3). Int J Stroke 12, 896-905 (2017).

Tong, D. et al. Times from symptom onset to hospital arrival in the Get with the Guidelines—Stroke Program 2002 to 2009: temporal trends and implications. Stroke; a journal of cerebral circulation 43, 1912-1917 (2012).

Mokin, M. et al. ASPECTS decay during inter-facility transfer in patients with large vessel occlusion strokes. Journal of NeuroInterventional Surgery (2016). doi:10.1136/neurintsurg-2016-012331.

Sun, C.-H. J. et al. ASPECTS decay during inter-facility transfer predicts patient outcomes in endovascular reperfusion for ischemic stroke: a unique assessment of dynamic physiologic change over time. Journal of NeuroInterventional Surgery 7, 22-26 (2015).

Van Seeters, T. et al. CT angiography and CT perfusion improve prediction of infarct volume in patients with anterior circulation stroke. Neuroradiology 58, 327-337 (2016).

Coutts, S. B. et al. ASPECTS on CTA Source Images Versus Unenhanced CT: Added Value in Predicting Final Infarct Extent and Clinical Outcome. Stroke; a journal of cerebral circulation 35, 2472-2476 (2004).

Bhatia, R. et al. CT Angiographic Source Images Predict Outcome and Final Infarct Volume Better Than Noncontrast CT in Proximal Vascular Occlusions. Stroke; a journal of cerebral circulation 42, 1575-1580 (2011).

Isola, P., Zhu, J.-Y., Zhou, T. & Efros, A. Image-to-Image Translation with Conditional Adversarial Networks. arXiv:1611.07004v1 1-16 (2016).

\* cited by examiner

SYSTEMS AND METHODS FOR EVALUATING THE BRAIN AFTER ONSET OF A STROKE USING COMPUTED TOMOGRAPHY ANGIOGRAPHY

CROSS-REFERENCE TO RELATED APPLICATION

This application is a continuation of, and claims priority to, co-pending U.S. Utility patent application Ser. No. 17/572,564, filed Sep. 16, 2019, and claims priority to co-pending U.S. Provisional Application Ser. No. 62/731,108, filed Sep. 14, 2018, which are both hereby incorporated by reference herein in their entirety.

BACKGROUND

Endovascular stroke therapy (EST) is one of the most significant advances in acute ischemic stroke (AIS) care in recent history. EST involves the physical removal of a thrombus from an artery in the brain to restore blood flow to ischemic brain tissue. Recent trials have demonstrated that patient disability after stroke can be reduced if EST is performed on an eligible patient within the first 24 hours of stroke symptoms. Accordingly, it is critical to determine within that time period whether or not a stroke patient is a candidate for EST.

The preferred method of evaluating the brain for purposes of determining whether or not to perform EST is to perform perfusion imaging (PI), which typically involves analyzing computed tomography perfusion (CTP) or magnetic resonance imaging (MRI) images. While PI images can be used to determine the amount of dead brain tissue and brain tissue at risk of dying, most hospitals do not have the capability to perform PI 24 hours a day as it requires specialized equipment, software, and training. As a consequence, stroke patients who could benefit from EST are not always treated with such therapy.

In view of the above discussion, it can be appreciated that there is a need for a way to evaluate the brain after onset of a stroke to determine eligibility for EST without having to perform PI.

BRIEF DESCRIPTION OF THE DRAWINGS

The present disclosure may be better understood with reference to the following figures. Matching reference numerals designate corresponding parts throughout the figures, which are not necessarily drawn to scale. The patent or application file contains at least one drawing executed in color. Copies of this patent or patent application publication with color drawing(s) will be provided by the Office upon request and payment of the necessary fee.

DETAILED DESCRIPTION

As described above, there is a need for a way to evaluate the brain after onset of a stroke to determine eligibility for endovascular stroke therapy (EST) without having to perform perfusion imaging (PI), which typically requires use of computed tomography perfusion (CTP) or magnetic resonance imaging (MRI). More particularly, there is a need for a way to perform such an evaluation based upon images captured using an imaging protocol that is more commonly available at most hospitals. Disclosed herein are systems and methods for evaluating the brain after onset of a stroke and, therefore, determining eligibility for EST, that are based on computed tomography angiography (CTA) images. As most hospitals are able to perform CTA, the disclosed systems and methods enable more patients to be evaluated within the 24-hour critical period and, therefore, enable more eligible patients to receive EST. In some embodiments, a system for evaluating the brain after onset of a stroke comprises a computer program that analyzes CTA images to assess various parameters associated with the stroke and the patient's eligibility for EST. With such information, a medical professional (e.g., surgeon) can make a determination as to whether or not EST should be performed. In some embodiments, the program leverages a machine-learning algorithm that has been trained using the results of PI image analysis software. In such a case, results comparable to those based upon PI images can be obtained using CTA images.

In the following disclosure, various specific embodiments are described. It is to be understood that those embodiments are example implementations of the disclosed inventions and that alternative embodiments are possible, including alternative embodiments that include features from different embodiments. All such embodiments are intended to fall within the scope of this disclosure.

Figure 1:
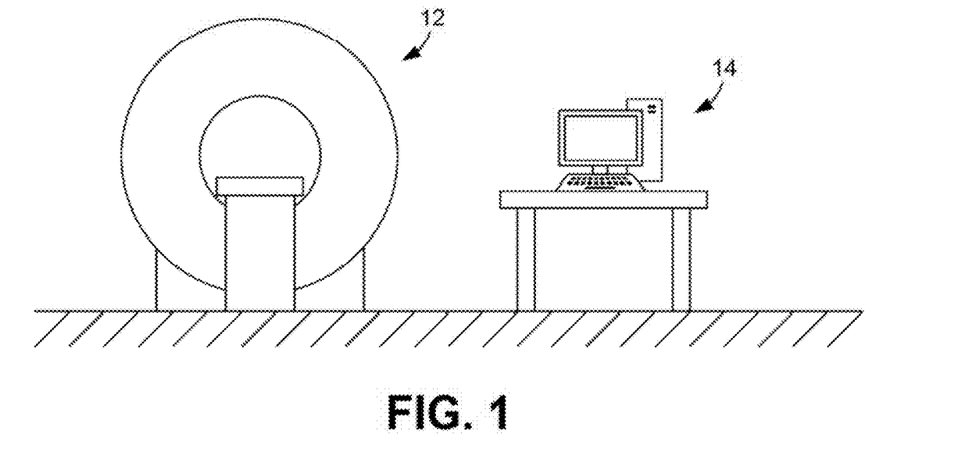
FIG. 1 is schematic view of an embodiment of a system for evaluating the brain after onset of a stroke based on computed tomography angiography (CTA).

FIG. 1 illustrates an example system 10 for evaluating the brain after onset of a stroke using CTA. As shown in the figure, the system 10 generally includes a computed tomography (CT) machine 12 that is capable of capturing CTA images and a computing device 14 in electrical communication with the CT machine that can control operation of the machine and perform analysis on CTA images captured by the machine to assess an ischemic core and related phenomena.

Figure 2:
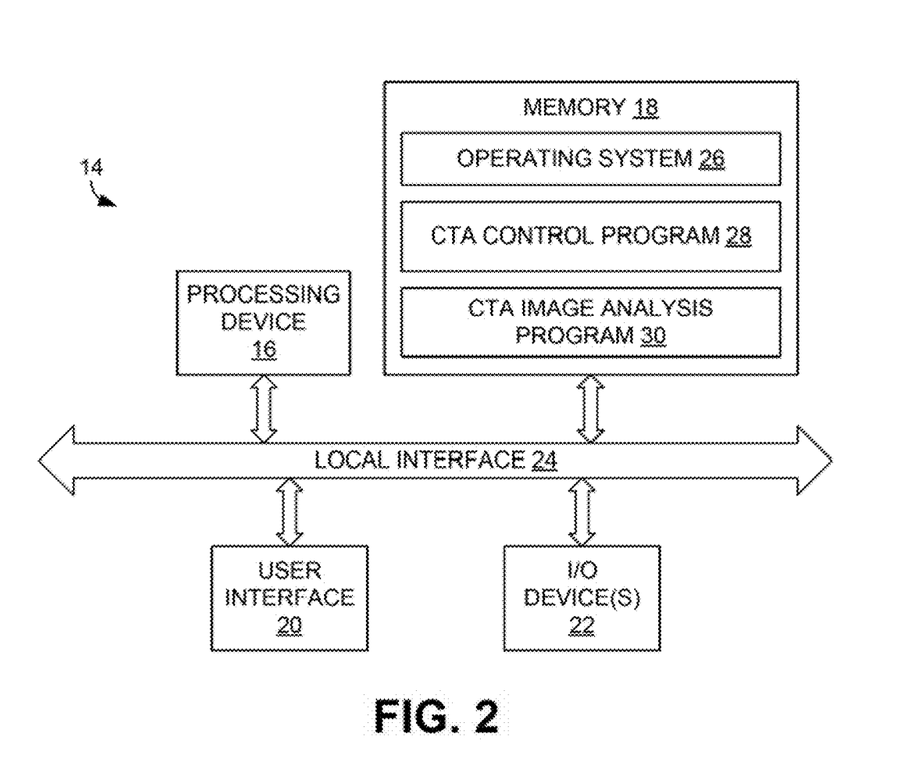
FIG. 2 is a block diagram of an embodiment of a computing device shown in FIG. 1.

FIG. 2 is a block diagram of an example embodiment for the computing device 14 shown in FIG. 1. The computing device 14 generally comprises a processing device 16, memory 18, a user interface 20, and one or more input/output (I/O) devices 22, each of which being connected to a system bus 24. The processing device 16 can, for example, include a central processing unit (CPU) that is capable of executing computer-executable instructions stored within the memory 18. The memory 18 can include any one of or a combination of volatile memory elements (e.g., RAM, flash, etc.) and nonvolatile memory elements (e.g., hard disk, ROM, etc.).

The user interface 20 can comprise one or more devices that can enter user inputs into the computing device 14, such as a keyboard and mouse, as well as one or more devices that can convey information to the user, such as a display. The I/O devices 22 can comprise components that enable the computing device 14 to communicate with other devices, such as a network adapter and a wireless transceiver. While particular components are illustrated in FIG. 2, it is noted that the computing device 14 need not comprise each of these components and can comprise other components. For example, the computing device 14 can further comprise a graphical processing device, such as a graphical processing unit (GPU).

In the illustrated example, the memory 18 (a non-transitory computer-readable medium) stores executable programs (software) including an operating system 26, a CTA control program 28, and a CTA image analysis program 30. Each of the programs includes computer-executable instructions, which may be comprised by one or more algorithms (i.e., computer logic), that can be executed by the processing device 16. The operating system 26 controls the general operation of the computing device 14, while the CTA control program 28 controls operation of the CT machine 12 and receives CTA images that can be analyzed by the CTA image analysis program 30. The CTA image analysis program 30 is configured to analyze CTA images to evaluate the brain after onset of a stroke and provide information that may be relevant to the determination as to whether or not EST is advisable for the patient. In some embodiments, the CTA image analysis program 30 incorporates a machine-learning algorithm that has been trained using the results of PI image analysis so that the CTA image analysis program is capable of generating results comparable to those that would be generated by existing PI analysis software.

Figure 3:
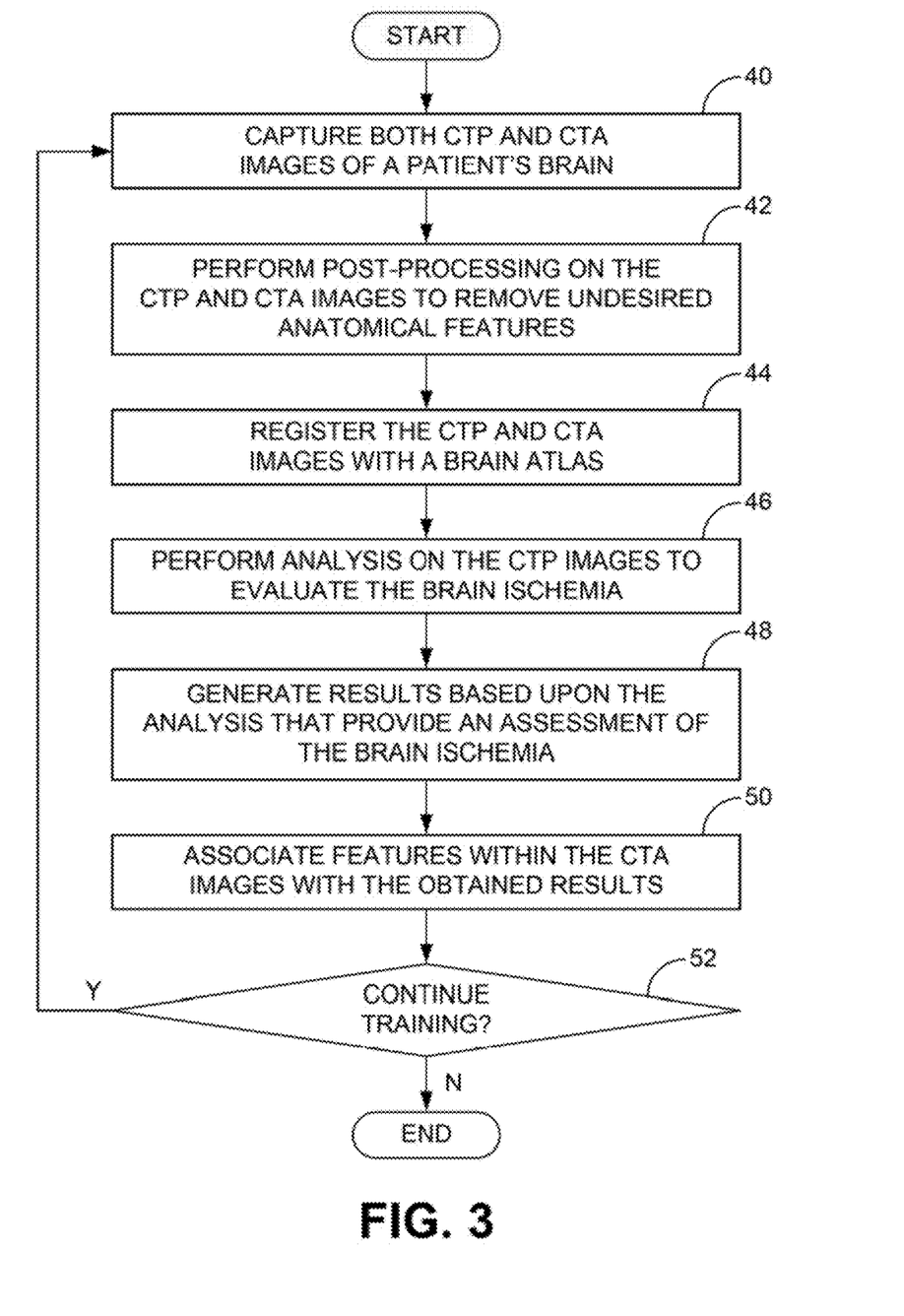
FIG. 3 is a flow diagram of an embodiment of a method for training a CTA image analysis program.

FIG. 3 is a flow diagram that illustrates an example method for training the CTA image analysis program so that it can evaluate the brain after onset of a stroke in a manner similar to PI analysis software. Beginning with block 40, both PI and CTA images are captured for a given stroke patient within 24 hours of the onset of stroke symptoms. In some embodiments, capturing PI images comprises capturing multiple PI scans, each scan comprising multiple images that represent slices of the brain, over a predetermined period of time as an injected contrast agent flows through the cerebral arteries. In some embodiments, capturing CTA images comprises capturing a single scan, also comprising multiple images that represent slices of the brain, when an injected contrast agent is within the cerebral arteries. Regardless, the two sets of images (i.e., a PI image set and a CTA image set) are acquired close in time to each other so as to enable correlation between the images and the results they reveal.

Referring next to block 42, post-processing can be performed on both the PI and CTA images to remove any undesired anatomical features present in the images. Such features can, for example, comprise bones and blood vessels, although, as described below, the latter may be useful in performing the analysis. The processed images can then be registered with an atlas of the brain to identify the orientation of the brain, as indicated block 44.

With reference next to block 46, analysis can be performed on the PI images to evaluate the brain after onset of a stroke. Various parameters associated with the stroke and the patient's eligibility for EST can be determined through this analysis. Such parameters can include one or more of the extent (e.g., volume) of an existing infarction (ischemic core), the amount of tissue (e.g., volume) at risk of infarction, the presence or absence of a large vessel occlusion (LVO), and the presence or absence of brain hemorrhage. Such analysis can be performed using a commercial analysis program, such as the CTP-RAPID® software package (IschemaView, Stanford, Calif.). When this analysis is performed, results are generated that provide an assessment of the patient's brain (block 48), which assists the medical professional in making a determination as to whether or not to perform EST.

Figure 4:
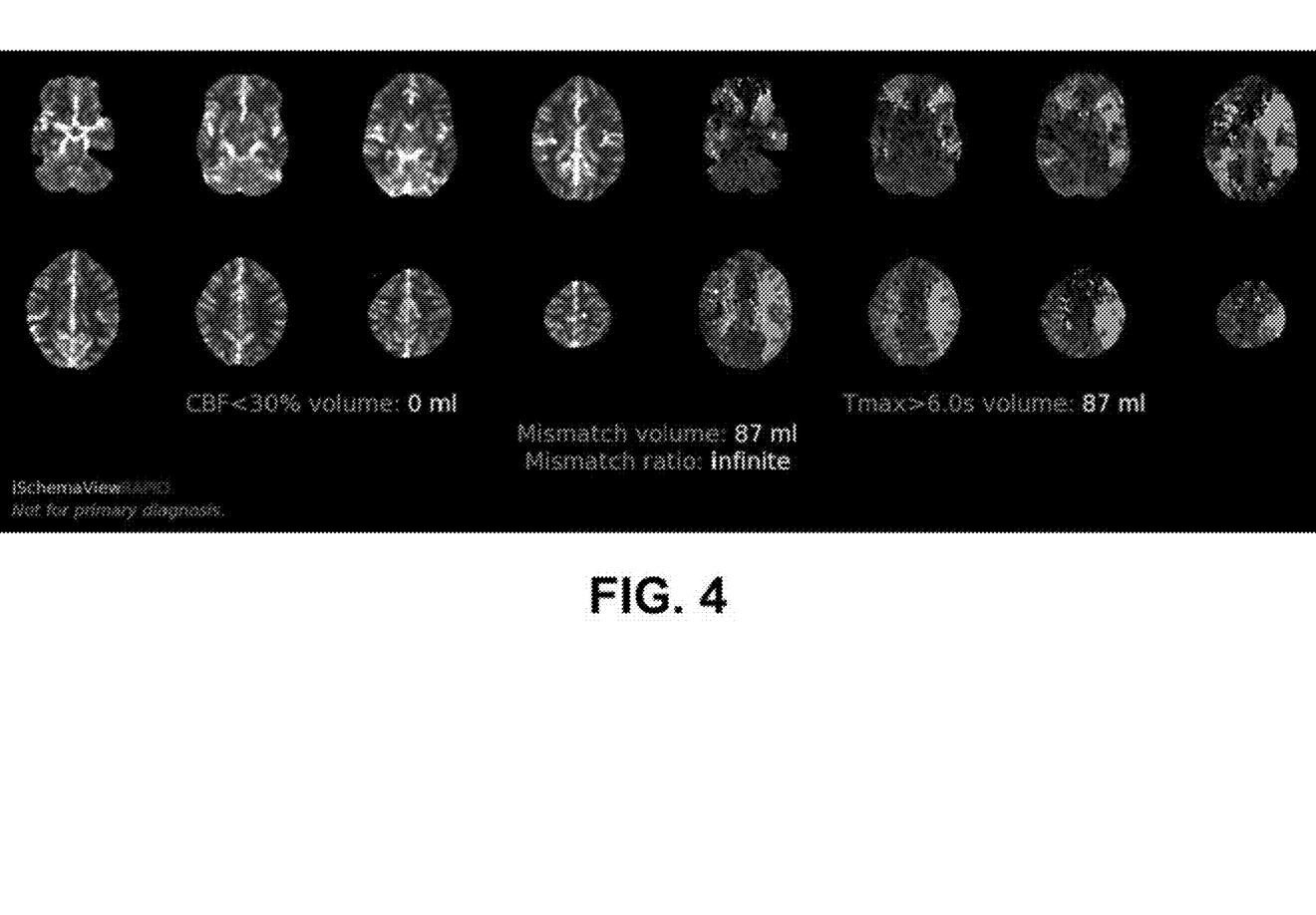
FIG. 4 is an example output of a computed tomography (CT) perfusion analysis program.

FIG. 4 provides one example of results that can be produced by such analysis. In particular, FIG. 4 shows a graphical output that includes a series of PI images of various vertical slices of the brain that identify both necrotic and at-risk brain tissue. In this example, the 8 images on the left identify dead tissue with a pink color and the 8 images on the right identify at-risk tissue with a green color. Such a visual representation gives the medical professional an idea of the amount and location of the damage as well as an idea of which and how much tissue could potentially be saved if EST were performed. In addition to these visual representations, the output shown in FIG. 4 also includes estimates of the volume of dead tissue and the volume of at-risk tissue. In this example, it is estimated that there is 0 ml of dead brain tissue (based upon relative cerebral blood flow (CBF) being below 30%) and 87 ml of at-risk brain tissue (based upon the $T_{max}$ indicator being greater than 6 seconds). In other embodiments, the results of the PI image analysis can additionally comprise an indication of the presence or absence of an LVO and/or the presence or absence of brain hemorrhage. In still further embodiments, the results of the PI image analysis can also include an explicit indication as to whether or not EST is advised. Such an indication can, for example, comprise a simple "treat" or "do not treat" indication (or equivalent), or could comprise some form of qualitative measure as to the advisability of EST.

Irrespective of the nature of the results obtained through the PI image analysis, the goal is to be able to generate results comparable to those obtained using PI but based solely on CTA images. To that end, a machine-learning algorithm of the CTA image analysis program associates features within the CTA images with the results obtained by analyzing the PI images, as indicated in block 50. An example machine-learning algorithm, as well as experimental results obtained using that algorithm, are described in detail below. When the above-described process is performed multiple times for multiple patients and multiple sets of PI and CTA images, the algorithm learns what results would be reached by analyzing PI images by analyzing the features of CTA images. Accordingly, similar results can be achieved without having to perform PI.

Flow at this point depends upon whether or not training is complete. If not, flow returns to block 40 and PI and CTA images are captured from the next stoke patient. The process continues in this manner until the CTA image analysis program is capable of generating comparable results to those obtained by analyzing PI images. In such a case, the CTA analysis can be performed as a proxy for the PI analysis.

Figure 5:
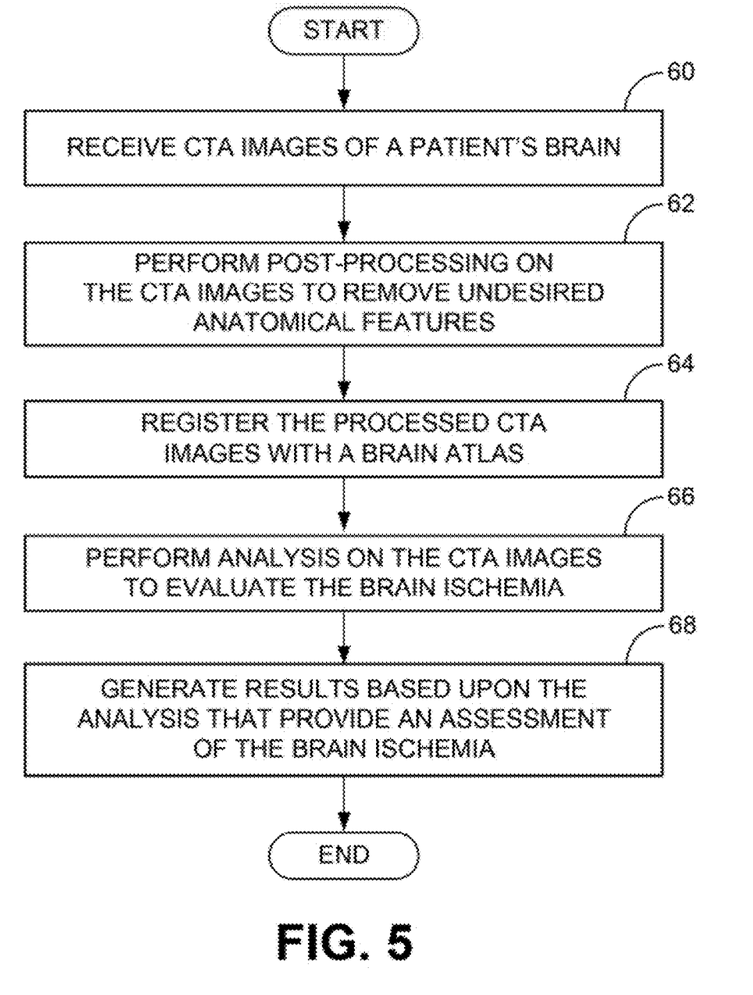
FIG. 5 is a flow diagram of an embodiment of a method for analyzing CTA images to evaluate the brain after onset of a stroke.

Once the CTA image analysis program has been trained, it can be used as a tool for assisting medical professionals in making determinations as to whether or not stroke patients should receive EST. FIG. 5 is a flow diagram that illustrates the operation of the CTA image analysis program in that capacity. Beginning with block 60, CTA images are captured for a new stroke patient within 24 hours of the onset of symptoms. As noted above, capturing CTA images can comprise capturing a single scan that includes multiple images (slices) when an injected contrast agent reaches the cerebral arteries. Post-processing can then be performed on the CTA images to remove any undesired anatomical features present in the images (block 62) and the processed images can be registered with an atlas of the brain (block 64). Although not identified in FIG. 5, further processing can also include comparing the left hemisphere of the brain to the right hemisphere of the brain to enhance the ischemic core that exists in one of the hemispheres. An example of this is also described below.

With reference next to block 66, analysis can be performed on the CTA images to evaluate the patient's brain. As described above, various parameters associated with the stroke and the patient's eligibility for EST can be determined, such as one or more of the extent (e.g., volume) of an existing infarction (ischemic core), the amount of tissue (e.g., volume) at risk of infarction, the presence or absence of an LVO, and the presence or absence of brain hemorrhage. These determinations are based upon the training of the machine-learning algorithm of the CTA image analysis program described in relation to FIG. 3. Once the analysis has been performed, results are generated that provide an assessment of the patient's brain, as indicated in block 68. These results can be similar to those described above that were obtained by analyzing PI images. Accordingly, the results can, for example, comprise one or more of a series of CTA images of vertical slices of the brain that identify both necrotic and at-risk tissue, an indication of the presence or absence of an LVO, the presence or absence of brain hemorrhage, and an indication as to whether or not EST is advised. Irrespective of the particular nature results that are generated, the medical professional can then make a determination as to whether or not EST should be performed on the patient.

A novel convolutional neural network (CNN) referred to as the Deep Symmetry-Sensitive Convolutional Neural Network, or DeepSymNet, was created by the inventors and a study was performed at the University of Texas Health Science Center (UTHSC) at Houston, Tex., to evaluate its ability to identify LVOs as well as infarct cores from CTA images using CTP-RAPID® definitions. The study population comprised 2 groups of patients. Control patients were defined as patients who presented to the UTHSC Emergency Department for acute stroke evaluation, underwent full neuroimaging evaluation as described below, but were ultimately diagnosed as not having AIS or transient ischemic attack (TIA). For this population, a consecutive cohort of patients from January 2018 to March 2018 was identified. The second group of patients comprised patients who were diagnosed with AIS or TIA after evaluation by an inpatient stroke neurology service at UTHSC. These patients were identified from a prospectively maintained stroke program database from January 2016 to March 2018. Patients with and without LVOs were included. This database prospectively records all patients admitted with a stroke or TIA and captures demographic, clinical, radiographic, and outcome data.

All patients presenting to the Emergency Department for an acute stroke evaluation underwent the same neuroimaging protocol, which consists of a non-contrast head CT (NCHCT) followed by CTP and CTA. As such, an identical imaging protocol was performed in patients who were ultimately diagnosed with LVO AIS or non-LVO AIS, as well as those ultimately diagnosed as not having AIS or TIA. Post-processing of the CTP images was performed using CTP-RAPID® and default parameters that define an ischemic core as relative CBF reduction of least 30% of the contralesional hemisphere. Imaging data was gathered in a retrospective fashion, and CTA acquisition protocols were not altered in any way from the standard of care. CTAs were acquired using a standard single-phase acquisition technique.

Because the purpose of the study was to train and validate a machine-learning approach to stroke neuroimaging, the cohort of patients in the second group was balanced to contain comparable numbers of patients with small, moderate, and large-sized ischemic cores at presentation. A total sample size of approximately 300 patients was targeted, with roughly ⅔ of the patients having stroke and ⅓ as non-stroke.

Patients were excluded from the study for incomplete neuroimaging. In addition, patients were excluded if their neuroimaging contained significant motion artifacts or were otherwise of inadequate quality, including large-volume old infarcts or implanted materials, such as ventriculo-peritoneal shunts or aneurysm coils. Finally, patients with posterior circulation occlusions were excluded as these regions are incompletely evaluated by CTP.

Two primary end points were chosen to reflect questions that the AIS neuroimaging evaluation should address. The first end point was accuracy in the detection of LVO. LVO was defined as endovascularly accessible vessel occlusions that would be potentially amenable to EST, i.e., those within the intracranial internal carotid artery, M1 and M2 segments of the middle cerebral artery, and A1 and A2. As mentioned above, patients with vertebral, basilar, or posterior cerebral artery occlusions were excluded. The presence or absence of LVO was determined by expert interpretation of the raw CTA images.

The second primary end point was accuracy in detection of small ischemic cores. To this end, ischemic core was defined as the CTP-RAPID®-based ischemic core measurements (relative cerebral blood flow <30%) from the CTP images. This end point was first evaluated in a dichotomous fashion and cutoffs were chosen to coincide with criteria from the DAWN trial, a recent large study examining CTP-RAPIDe-predicted ischemic core-based selection of patients for EST. As such, the 2 dichotomous end points consisted of ischemic cores≤30 mL and ischemic cores≤50 mL. In sensitivity analysis, these end points were examined in patients presenting in the early time window (0-6 hours) and late time window (6-24 hours) separately. Finally, the ability of the machine-learning method to predict CTP- RAPID® ischemic core volume determinations as a continuous variable using correlation analysis was also evaluated.

DeepSymNet was designed to leverage brain symmetry information to learn particular outcome variables, for example, the presence of LVO and ischemic core volume. DeepSymNet analyzes the symmetry information in CTA images of the brain to determine if the patient has suffered from AIS, without needing the location of the areas affected. Inspired from the observation that the two hemispheres of the brain are visibly different in CTA images both in terms of vasculature structures as well as voxel intensities in the tissue affected by the stroke, the network robustly compares the two hemispheres of the patient's brain, both in the presence and in the absence of blood vessels in the images, to identify if a patient has suffered from AIS. Qualitative analysis of the network is also performed by visualizing the network activation for CTA images of AIS patients. The analysis confirms that the network learns to identify blood vessels and tissue structures in one hemisphere of the brain that are not present in the other hemisphere, thereby indicating a diagnosis of AIS. The mathematical basis for DeepSimNet is described in paragraphs that follow.

Given brain CTA volumes, $V_i$, with labels, $C_i \in \{0,1\}$, i=1, 2, . . . , n, the goal is to learn a mapping $V_i \to C_i$ that correctly classifies a brain CTA volume as having a stroke ($C_i$=1) or no stroke ($C_i$=0). DeepSymNet learns the asymmetry between the CTA volumes of the two hemispheres of a brain in order to detect AIS. This approach is inspired from the clinical observation that, typically, in the event of an ischemic stroke, blood vessels in one hemisphere of the brain are likely to be occluded while those in the other hemisphere are less affected. Consequently, observable differences in vasculature and brain tissue structure are seen in the two hemispheres of brain from CTA images.

An inception module is a combination of parallel convolutional layers that can be used as a building block for constructing deep neural networks, which have the ability to learn complex patterns in data. The module uses 1×1, 3×3, and 5×5 convolutions, along with max pooling, enabling the network to learn patterns at different scales from the different filter sizes used in parallel. Here, three-dimensional inception modules (i.e., three-dimensional versions of the filters: convolutions with kernels of size 1×1×1, 3×3×3, and 5×5×5) and three-dimensional max pooling are used since the data comprises three-dimensional volumes. The relationship between the input, $T_{IM}$, and output, $O_{IM}$, of an inception module is given by, $$O_{IM} = \{f_1^n \otimes \mathcal{I}_{IM}\} \oplus \{f_3^n \otimes (f_1^n \otimes \mathcal{I}_{IM})\} \oplus \{f_5^n \otimes (f_1^n \otimes \mathcal{I}_{IM})\} \oplus \{f_1^n \otimes P_3^{max}(\mathcal{I}_{IM})\} \quad (1)$$

where $f_k^n$ denotes n convolutional filters of kernel size k along each dimension, $P_k^{max}$ denotes max pooling with kernel size k along each dimension, $\otimes$ denotes convolution, and $\oplus$ denotes concatenation of filter outputs of same dimensions.

A Siamese Network is a neural network architecture that uses identical neural networks with identical weights to learn the similarities and differences between two inputs. Originally proposed for signature verification, it has been used for various computer vision applications. Although most networks employ a cost function to compare the outputs of the two identical networks for different inputs, a significantly different approach has been used here that employs convolutional layers to learn the complex differences in structure that are embedded in the output of the identical networks learning the differences and the addition of an L-1 merge layer.

Figure 6:
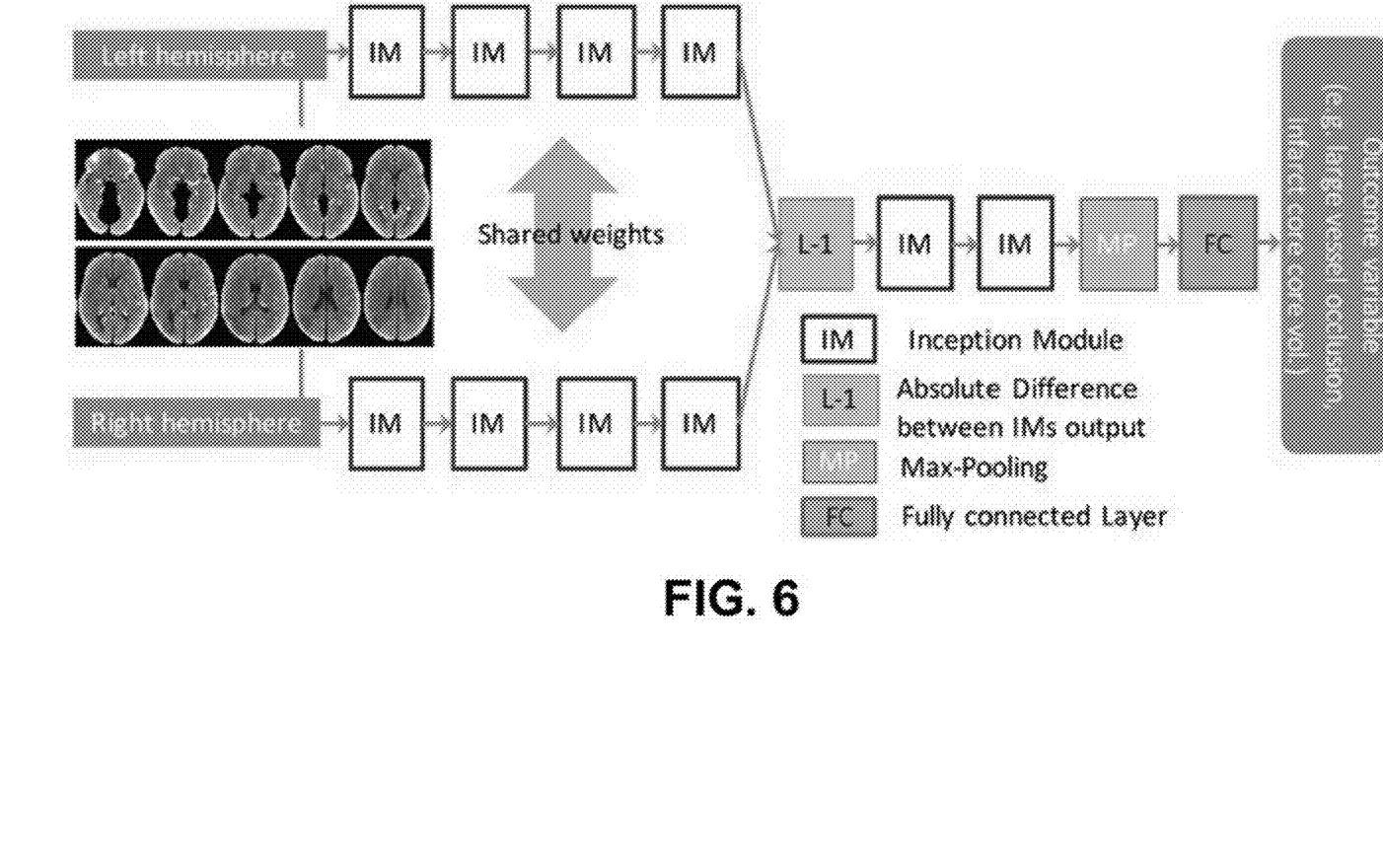
FIG. 6 is a schematic diagram that shows the architecture of the novel DeepSymNet convolutional neural network and its training based upon symmetry-sensitive relationships.

DeepSymNet is designed to take the CTA images of the two hemispheres of the brain as its inputs. The right hemispheres were flipped to facilitate the network learning process. The architecture of DeepSymNet is shown in FIG. 6.

Two identical convolutional neural networks having identical weights were used for learning the low- and high-level volume three-dimensional representations common to the two brain hemispheres. This convolutional neural network architecture employs 4 three-dimensional inception modules, one after the other. Then, instead of the commonly used approach of directly comparing differences with a cost function (such as contrastive loss), a markedly different method is used. Specifically, a "merge layer" was created that calculates the absolute difference (L-1 difference) between the high-level convolution filter outputs common to the two hemispheres. These differences contain crucial information about the asymmetry of the two hemispheres that cannot be accounted for using a simple loss function. Hence, the network is enabled to learn the information in the hemisphere differences by adding two additional inception modules to the architecture. The outputs from the final inception module are then max pooled and connected to the output prediction layer through a fully connected layer. The L-1 merge layer enables the network to equally weigh stroke visual patterns generated from the left or right hemisphere, and further enables the additional inception modules to learn convolutional filters sensitive to high-level differences.

In the model, 64 filters of each size were used in each of the inception modules. The entire network uses ReLU activations, except for the prediction layer that uses sigmoid activation. Finally, the loss function used is binary cross-entropy, which is given by, $$J(y, \hat{y}) = -\sum_i \{y_i \log \hat{y}_i + (1 - y_i) \log(1 - \hat{y}_i)\} \quad (2)$$

where $y_i$ and $y_i$ are the actual class and the predicted class, respectively. The optimizer used for our experiments is Adam with a learning rate of $1 \times 10^6$ for 40 epochs.

In the study, DeepSymNet was trained and tested using a 10-fold cross-validation on 2 binary variables: presence/absence of LVO and a dichotomized ischemic core size with a threshold of 30 or 50 mL. The DeepSymNet probabilities for the 2 binary variables were then used for the statistical analysis. The contribution of each voxel toward reaching the output classifier probability was evaluated using c-layerwise relevance propagation.

Univariate comparisons between continuous variables were performed using a Student's t test or Wilcoxon rank-sum testing for abnormal data, and univariate comparisons of categorical variables were performed using the Fisher exact test. From the DeepSymNet probabilities described above for the 3 comparisons (LVO detection, ischemic core≤30 mL, and ischemic core≤50 mL), receiver-operator curve analysis was performed, and DeepSymNet determinations were evaluated using AUC measurements with 95% confidence intervals (Cis). Correlation between DeepSymNet probabilities and CTP-RAPID® ischemic core volume predictions (as a continuous variable) was performed using Pearson correlation. The data is presented as mean±SD or median (interquartile range) unless otherwise specified. Analyses were performed using the Scikit-Learn/

Statsmodels Python libraries and confirmed with Stata/MP 14 (StataCorp LLC, College Station, Tex.), Prism 7 (GraphPad, La Jolla, Calif.) statistical software.

Among the 297 patients who met the inclusion criteria for the study, the median age was 67 and 50% were female. 224 total patients ultimately diagnosed with AIS were included, and 73 who underwent an acute stroke evaluation but did not have AIS. The non-stroke subgroup was younger (63 versus 69; P<0.01). The proportion of patients with LVO was intentionally enriched in this population, as described above, and LVO was present in 179 patients (60%). Among patients diagnosed with AIS, the occlusion location was intracranial (ICA) in 13%, M1 middle cerebral artery (MCA) in 44%, and M2 MCA in 21%. Median ASPECTS was 9 (7-10). Among patients with AIS, 157 (70%) presented within the early time window 6 hours) and the rest presented in the late time window (between 6 and 24 hours). Among patients with LVO, 124 (69%) were found on CTP-RAPID® imaging to have ischemic core volume of ≤30 mL and 143 (80%)≤50 mL.

Figure 7:
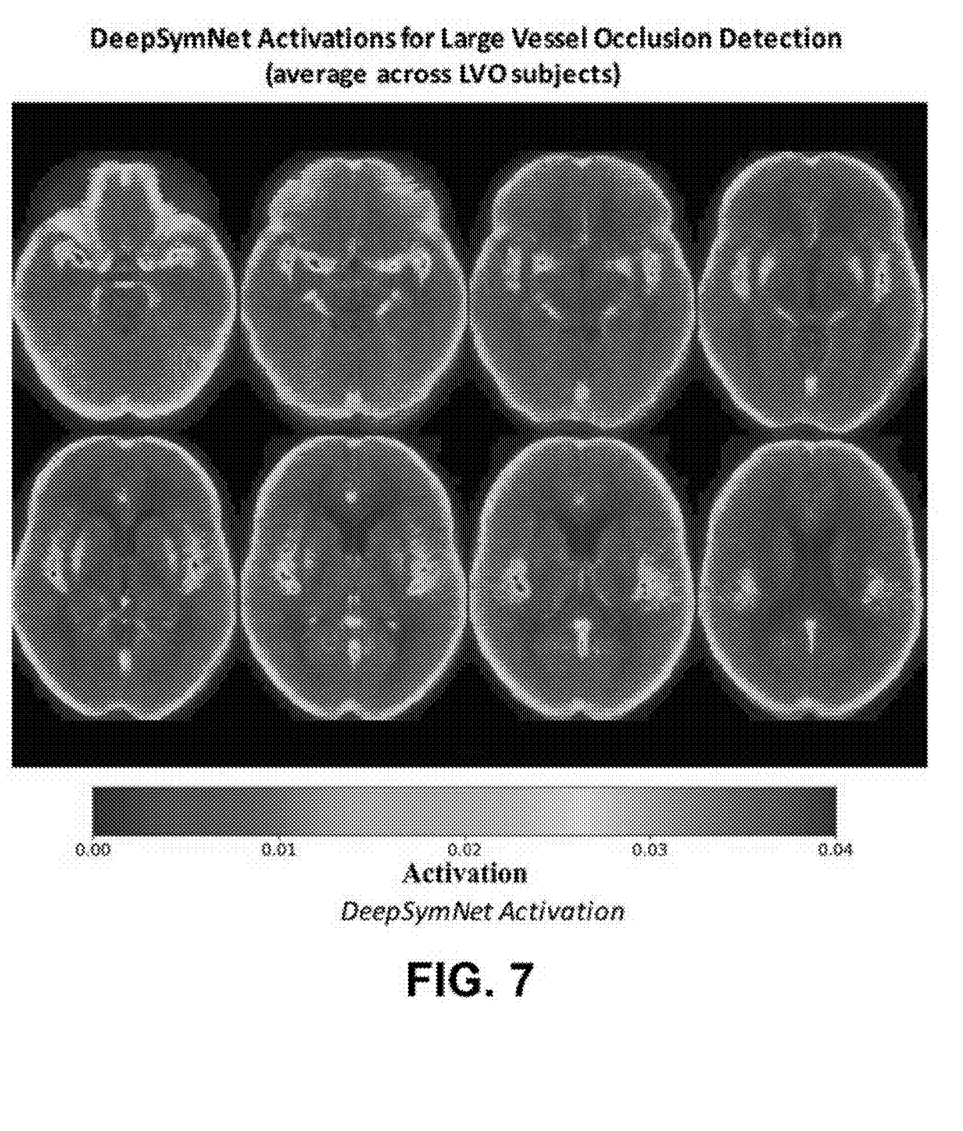
FIG. 7 includes multiple CTA images that identify DeepSymNet activation zones for a large vessel occlusion (LVO) identification task. Color mapping indicates the magnitude of the contribution to the LVO determination.

Using this dataset, the trained DeepSymNet was then used to evaluate the regions on the images that lead to the algorithm's decisions. FIG. 7 demonstrates the average activation zones leading to decision making in a DeepSymNet model trained on discriminating between LVO and non-LVO for the full cohort. The model was strongly activated by the regions of the image corresponding to the vasculature.

Figure 8A:
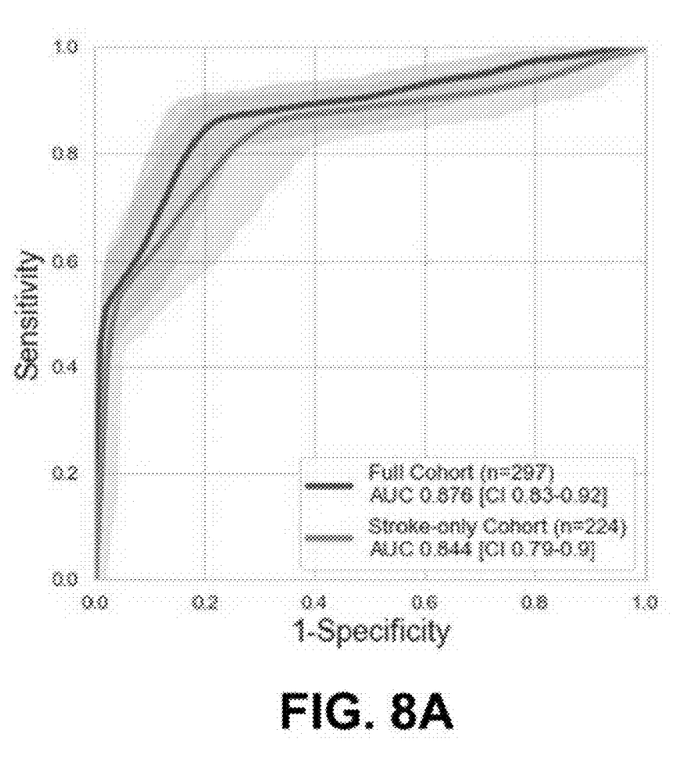
FIG. 8A is a graph that plots receiver-operating sensitivity curves for the detection of LVO using DeepSymNet.
Figure 8B:
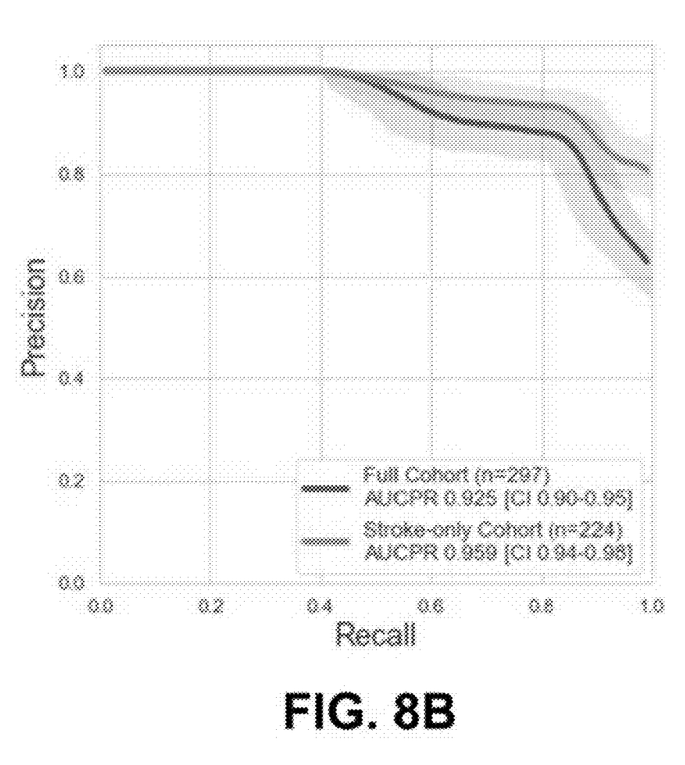
FIG. 8B is a graph that plots receiver-operating precision curves for the detection of LVO using DeepSymNet.

The performance of DeepSymNet predictions was then evaluated across the entire cohort (LVO AIS, non-LVO AIS, and stroke mimics). Examined first was the ability of the algorithm to discriminate between LVO and non-LVO (non-LVO AIS and stroke mimic). As shown in FIG. 8, the model performed with AUC 0.88 (0.83-0.92; 95% CI) for the full cohort and AUC 0.84 (0.79-0.9; 95% CI) for LVO AIS and non-LVO AIS.

Figure 9A:
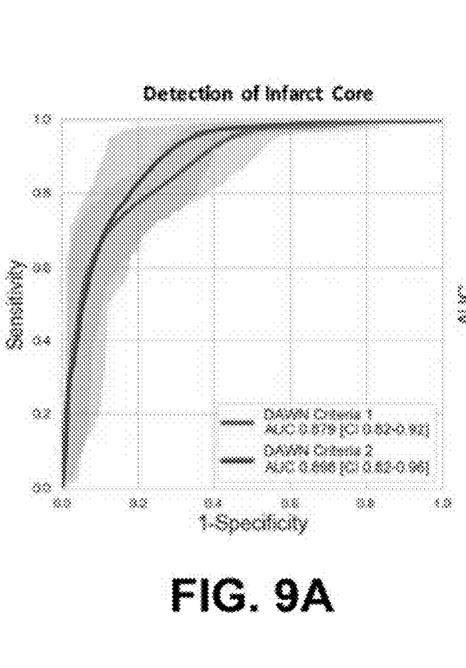
FIG. 9A is a graph that plots curves and corresponding areas-under-the-curve (AUCs) for the DeepSymNet performance in identifying infarct core≤30 mL (DAWN Criteria 1) and infarct core≤50 mL (Dawn Criteria 2) as determined by CTP-RAP ID®.
Figure 9B:
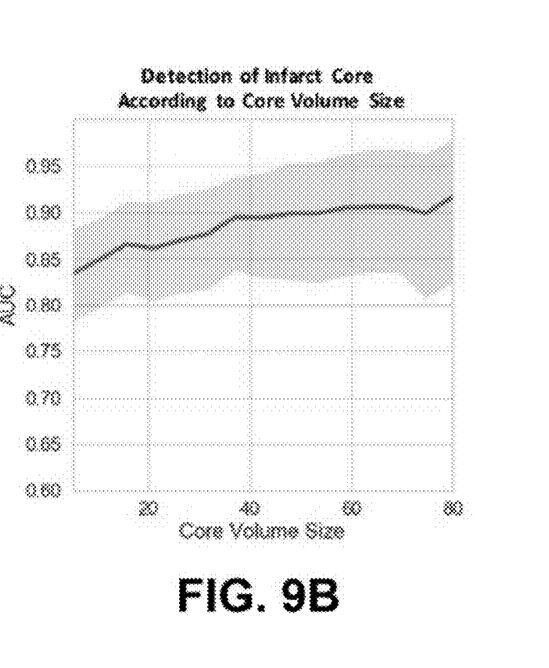
FIG. 9B is a graph that plots lines demonstrating the improving performance of DeepSymNet to identify ischemic cores by ischemic core volume. The dark green line represents a point estimate and the shaded green area represents the 95% confidence interval (CI).

The performance of the algorithm was next evaluated across the entire cohort to identify if the ischemic core as predicted by CTP-RAP ID® was 30 and 50 mL (DAWN Criteria 1 and DAWN Criteria 2). As shown in FIG. 9A, the algorithm performed similarly (AUC 0.88 [0.82-0.92, 95% CI] and 0.90 [0.82-0.96, 95% CI], DAWN Criteria 1 and DAWN Criteria 2). DeepSymNet discrimination performance of large versus small ischemic cores increased as a function of the ischemic core threshold used, as shown in FIG. 9B.

Figure 9C:
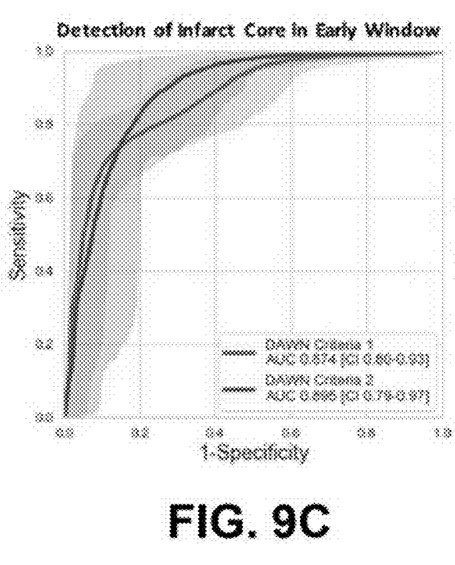
FIG. 9C is a graph that plots curves and corresponding AUCs for the DeepSymNet performance in identifying infarct cores≤30 mL (DAWN Criteria 1) and infarct cores≤50 mL (Dawn Criteria 2) in patients presenting in ≤6 hours.
Figure 9D:
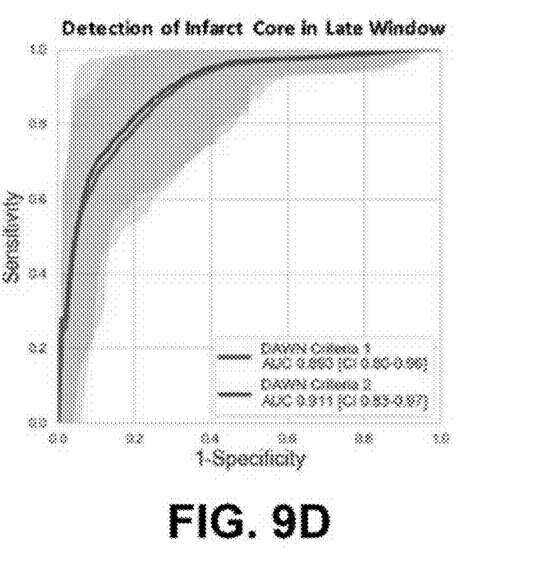
FIG. 9D is a graph that plots curves and corresponding AUCs for the DeepSymNet performance in identifying infarct cores≤30 mL (DAWN Criteria 1) and infarct cores≤50 mL (Dawn Criteria 2) in patients presenting in >6 hours and <24 hours from the last known well time.

In sensitivity analysis, the accuracy of DeepSymNet to predict ischemic core volume thresholds in patients presenting in the early and late time window was then separately determined. As shown in FIG. 9C, in the early time window, the performance of DeepSymNet remained stable (AUC 0.87 and 0.90, DAWN Criteria 1 and DAWN Criteria 2). This finding was also maintained in the subset of patients presenting in the late time window (AUC 0.89 and 0.91, DAWN Criteria 1 and DAWN Criteria 2), as shown in FIG. 9D.

While DeepSymNet was designed to identify dichotomous thresholds, the probabilities can be evaluated as continuous variables and correlated to continuous ischemic core measurements by CTP-RAPID®. DeepSymNet probabilities had an acceptable correlation against CTP-RAP ID® predictions of ischemic core (r=0.70 [0.63-0.75]; P<0.0001, Pearson correlation).

The above results demonstrate that the DeepSymNet algorithm exhibits high accuracy in identifying patients with LVOs as well as dichotomized measures of ischemic core, with AUCs greater than the threshold of 0.8 to define good performance in prior imaging biomarker studies. The algorithm autonomously learned to use disease-relevant areas to generate its predictions without any prior knowledge, building confidence in the methodology. These results demonstrate that much of the data needed to perform the neuroimaging evaluation for EST may be present in readily available imaging modalities, such as non-contrast head CT and CTA, as well as the potential for machine-learning approaches to automate these analyses.

While the foregoing disclosure has focused on obtaining results that assist a medical professional in determining whether or not EST should be performed, it is noted that the disclosed systems and methods can more generally be used to evaluate the brain after onset of a stroke whether or not the information gleaned from the evaluation is to be used to make an EST eligibility determination. Accordingly, the systems and methods can be used to evaluate a stroke patient's brain in substantially any context.

The invention claimed is:

1. A method for evaluating a stroke patient's brain, the method comprising:
   capturing computed tomography angiography (CTA) images of the stroke patient's brain;
   analyzing the captured CTA images with a machine learning-based algorithm that has been trained to quantify a size of an ischemic core based upon similar analysis that has been performed on computed tomography perfusion (CTP) images; and
   generating results based solely upon the analysis of the CTA images by the machine learning-based algorithm that provide an indication as to whether the stroke patient is eligible for endovascular stroke therapy (EST).

2. The method of claim 1, wherein capturing CTA images comprises capturing the CTA images within 24 hours of the patient experiencing the onset of stroke symptoms.

3. A non-transitory computer-readable medium that stores computer-executable instructions configured to:
   receive CTA images of a stroke patient's brain;
   analyze the CTA images with a machine learning-based algorithm that has been trained to quantify a size of an ischemic core based upon similar analysis that has been performed on computed tomography perfusion (CTP) images; and
   generate results based solely upon the analysis of the CTA images by the machine learning-based algorithm that provide an indication as to whether the stroke patient is eligible for endovascular stroke therapy (EST).

* * * * *